United States Patent [19]

Sebag

[11] Patent Number: 4,885,402

[45] Date of Patent: Dec. 5, 1989

[54] PROCESS FOR PREPARING NONIONIC SURFACTANTS FROM GLYCEROL MONOCHLOROHYDRIN, IN AN AROMATIC SOLVENT MEDIUM, PRODUCTS OBTAINED AND COMPOSITIONS CONTAINING THEM

[75] Inventor: Henri Sebag, Paris, France

[73] Assignee: L'Oreal, Paris, France

[21] Appl. No.: 201,742

[22] Filed: Jun. 3, 1988

[30] Foreign Application Priority Data

Jun. 5, 1987 [FR] France ............................. 87 07956

[51] Int. Cl.$^4$ ............................................. C07C 43/11
[52] U.S. Cl. .................................. 568/620; 568/619; 568/608
[58] Field of Search ....................... 568/619, 608, 620

[56] References Cited

U.S. PATENT DOCUMENTS 3,917,717 10/1988 Griscom ............................. 568/640

FOREIGN PATENT DOCUMENTS 1164529 10/1958 France .
2160976 7/1973 France .
2168348 3/1986 United Kingdom .
2168348A 6/1986 United Kingdom ................ 568/619

*Primary Examiner*—Joseph L. Schofer
*Assistant Examiner*—Jeffrey T. Smith
*Attorney, Agent, or Firm*—Cushman, Darby & Cushman

[57] ABSTRACT

Process for preparing polyglycerolated nonionic surfactants from (poly)hydroxylated organic compounds, by condensing glycerol monochlorohydrin with the said (poly)hydroxylated compound in the presence of a strong base, at a temperature below 150° C. and in the presence of an aromatic solvent, removing the water formed by distillation as it forms.

This process makes it possible to condense a relatively large quantity of glycerol monochlorohydrin in a single step, while limiting the formation of polyglycerols, and to obtain a good quality surfactant which is usable in cosmetic compositions.

12 Claims, No Drawings

PROCESS FOR PREPARING NONIONIC SURFACTANTS FROM GLYCEROL MONOCHLOROHYDRIN, IN AN AROMATIC SOLVENT MEDIUM, PRODUCTS OBTAINED AND COMPOSITIONS CONTAINING THEM

The present invention relates to a new process for preparing polyglycerolated nonionic surfactants, from glycerol monochlorohydrin and certain organic compounds containing at least one active hydrogen atom, in the presence of a strong base and an aromatic solvent.

French Patent Application No. 2,574,786 describes a process for preparing nonionic surfactants by the simultaneous addition of glycerol monochlorohydrin and a strong base, at a temperature above or equal to 150° C., to a (poly)hydroxylated compound, removing the water by distillation as it forms.

The reaction scheme may be written for a compound (I) containing i hydroxyl groups:

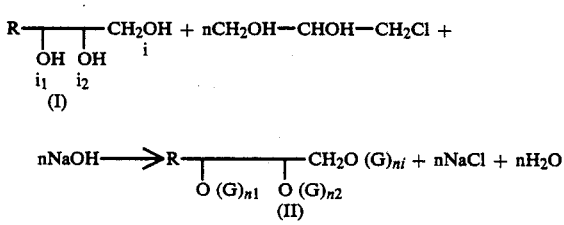

G denotes an arrangement of units having the following structures:

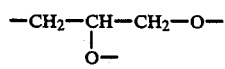

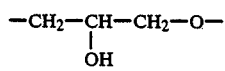

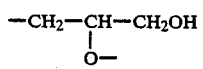

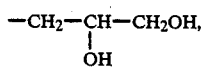

this structure being that of the terminal unit each of the symbols $n_1, n_2 \ldots n_i$ denoting, for each molecule, the number, integral or zero, of hydrophilic group(s) per hydroxyl group.

For one mole of (poly)hydroxylated compound, the sum $\Sigma n_1 + \Sigma n_2 \ldots + \Sigma n_i$ is an integral or decimal number less than or equal to n, n being the number of moles of glycerol monochlorohydrin used per mole of compound (I).

During the reaction, a fraction of the glycerol monochlorohydrin can hydrolyse or polymerize to form polyglycerols, which explains the fact that the sum $\Sigma n_1 + \Sigma n_2 + \ldots + \Sigma n_i$ of hydrophilic groups attached per mole of surfactants of formula (I) may be less than n.

The preparation process described in French Patent Application No. 2,574,786 presents a few problems of implementation, especially when the number of moles of glycerol monochlorohydrin per mole of hydroxyl compound, designated by n, exceeds approximately 3. In effect, the quantity of sodium chloride which forms and which precipitates increases as n increases, and the reaction medium becomes difficult to stir. To avoid these drawbacks, the process according to this patent application recommended working in two stages, that is to say condensing a first portion of the glycerol monochlorohydrin, removing the salt formed by filtration or washing and then resuming the condensation of the second portion of glycerol monochlorohydrin. Although these operations are simple in their principle, they represent considerable additional burdens and complications for an industrial process.

The applicants have discovered that it was possible to carry out the condensation in a single stage, even for a higher value of n (mole ratio of glycerol monochlorohydrin to the hydroxyl compound), while limiting the formation of polyglycerols. Polyglycerols, which originate from the polymerization and hydrolysis of glycerol monochlorohydrin, are not prejudicial to the properties of the nonionic surfactant formed, as long as the proportions remain relatively low. However, the formation of polyglycerols, which constitute by-products, takes place at the expense of the elongation of the hydrophilic chains linked to the polyhydroxylated compound containing a fatty chain, the consequence of this being a decrease in the solubility in water of the nonionic surfactant which it is sought to prepare.

Hence, for a given value of n, the smaller the quantity of polyglycerols, the more hydrophilic the non-ionic surfactants that will be obtained; this increase in hydrophilicity results in a greater solubility in water and in an increase in the cloud points.

The quantities of polyglycerols must be kept in small proportions, since they contain many hydroxyl groups capable of competing, during the reaction with glycerol monochlorohydrin, with the groups linked to the fatty chain, more especially since, as a result of their polarity, polyglycerols show greater affinity towards glycerol monochlorohydrin.

It has been discovered that the addition of an aromatic solvent to the (poly)hydroxylated compound surprisingly makes it possible to improve the reaction between the latter and glycerol monochlorohydrin, and at the same time to decrease the quantity of polyglycerols formed. The improvement is especially notable when the number n of moles of glycerol monochlorohydrin per mole of (poly)hydroxylated compound exceeds 3. It then becomes perfectly possible to condense up to 10 moles of glycerol monochlorohydrin per mole of (poly)hydroxylated compound (n=10) without it being necessary to work in several stages in order to remove the salt formed. Stirring of the reaction medium is readily accomplished, and this enables local concentrations of glycerol monochlorohydrin or of strong base to be avoided.

Under the conditions of the reaction, glycerol monochlorohydrin has a strong tendency to polymerize to form polyglycerols, and it is surprising to find that the addition of an aromatic solvent, according to the invention, enables the quantity of polyglycerols to be reduced and the yield of desired surfactants to be improved.

Preferred aromatic solvents are toluene, xylenes and cumene. It is preferable to use the commercial mixture of the three isomers, ortho-, meta- and para-xylene. The aromatic solvent is used at from 0.4 to 1.5 parts by weight, and preferably from 0.5 to 1 part, for 1 part by weight of (poly)hydroxylated compound employed.

The mole ratio of glycerol monochlorohydrin to the (poly)hydroxylated compound is greater than 1, and is preferably between 2 and 10.

Preferred (poly)hydroxylated compounds are chosen from:
- alkylphenols such as octylphenol and nonylphenol,
- polyethoxylated fatty alcohols containing 8 to 24 carbon atoms in the lipophilic chain,
- polyethoxylated alkylphenols such as polyethoxylated octyl- or nonylphenol containing from 2 to 20 oxyethyl units,
- $C_8$ to $C_{20}$ 1,2-alkanediols
- (poly)glycerol ethers of formula:

$$R_1-O-[C_3H_6O_2]_mH \quad (III)$$

in which:
$R_1$ denotes
- an octyl- or nonylphenol radical,
- a $C_8$ to $C_{24}$ aliphatic radical,
- an aliphatic or cycloaliphatic radical which can contain from 18 to 30 carbon atoms and is derived from hydrogenated lanolin or lanolin alcohols, and m denotes 1 or 2, or an average statistical number from 1.5 to 8.

The aliphatic radicals are preferably chosen from alkyl and alkenyl radicals.

(poly)glycerol ethers of formula:

$$R_2-O-[C_2H_3(CH_2R_3)O]_p[C_3H_6O_2]_qH \quad (IV)$$

in which:
$R_2$ denotes an octylphenyl or nonylphenol radical or a $C_8$ to $C_{24}$ aliphatic radical, and
$R_3$ denotes a $C_7$ to $C_{17}$ aliphatic radical or a $C_8$ to $C_{20}$ alkoxy radical, with the proviso that the sum of the carbon atoms in $R_1$ and $R_2$ is between 16 and 32,
the aliphatic radicals are preferably chosen from alkyl and alkenyl radicals,
p denotes the number 1 or an average statistical value of between 1.5 and 2, and
q denotes the number 1 or 2 or an average statistical value of 1.5 to 8.

The reaction temperature is below 150° C. It is between 120° and 145° C., and preferably between 130° and 145° C.

The use of a relatively small quantity of the aromatic solvent for dispersing the sodium chloride formed and the choice of a temperature below 150° C. contribute to reducing the overheating phenomena and to improving the quality of the surfactants obtained.

The (poly)hydroxylated compound is solubilized in the aromatic solvent in a reactor, and the mixture is heated to reflux under a stream of inert gas, preferably nitrogen. A solution of strong base, and preferably an aqueous NaOH (sodium hydroxide) or KOH (potassium hydroxide) solution, advantageously having a concentration of 35–40%, and glycerol monochlorohydrin are then introduced simultaneously from two different containers, in the space of 2 to 5 hours, according to the value of n.

The strong base is used in a stoichiometric quantity with respect to the glycerol monochlorohydrin, this quantity being from 5 to 10 mole % higher with respect to the (poly)hydroxylated compound.

The water is removed by azeotropic distillation.

After the addition of the strong base and the glycerol monochlorohydrin is complete, the reaction mixture is heated for 5 to 15 minutes, optionally with partial removal of the solvent used. The mixture is then cooled to about 70°–80° C. and taken up with an alcohol having 1 to 4 carbon atoms, and preferably with methanol, isopropanol or butanol, to separate off the sodium chloride.

After filtration, the aromatic solvent and the alcohol are distilled off at atmospheric pressure, and then under reduced pressure.

The surfactants obtained according to the process of the invention are more or less hydrophilic. They may be soluble or only dispersible in water, depending on the (poly)hydroxylated compound used and the number of moles of glycerol monochlorohydrin condensed per mole of (poly)hydroxylated compound.

They may be used in cosmetics, dermatology and paradermatology, as foaming, emulsifying or dispersing agents, or vehicles or excipients.

By virtue of their nonionic nature, they may be combined readily with the different base products or additives used for the care and treatment of the skin and hair. They may thus be combined with other nonionic, anionic, cationic, amphoteric or zwitterionic surfactants, with natural or synthetic polymers, with thickeners, foam synergists, opacifiers, pearlescent agents, sunscreens, natural or synthetic oils, sterols, lecithins, preservatives, colorings and perfumes, and with the other adjuvants customarily used in cosmetics.

The subject of the invention is also the surfactants prepared by the process according to the invention, as well as the compositions, and especially the cosmetic compositions, containing these surfactants.

The invention is illustrated by the following preparation examples.

EXAMPLE 1

50.5 g (0.25 mole) of 1,2-dodecanediol are heated to 128° C. in the presence of 25 g of toluene, under a stream of nitrogen. 91.5 g of an aqueous solution of NaOH with 9.7 meq/g of NaOH (0.887 mole) and 96.7 g (0.875 mole) of glycerol monochlorohdyrin are then added simultaneously, using two separate dropping funnels. The addition of NaOH is, carried out first, and steps are taken to maintain a basic medium at all times.

Duration of the additions: 3 hours 15 minutes.

The temperature is maintained between 130° and 145° C. and the water is removed, as it forms, by azeotropic distillation according to the Dean-Stark process.

Upon completion of the additions, the temperature is maintained constant for about 10 minutes, and then the reaction mixture is allowed to cool down to 80° C.

The reaction mass is taken up with 150 ml of isopropanol and the sodium chloride is then filtered off. The solvents are then removed by heating under reduced pressure.

A water-soluble, light brown product is thus obtained.

The cloud point, which is measured at a concentration of 0.5% by weight in water containing 25% by weight NaCl, is greater than 100° C.

EXAMPLE 2

101 g (0.05 mole) of 1,2-dodecanediol are heated to 135°–140° C. in 50 g of a commercial mixture of xylenes, under a light stream of nitrogen. Then, as in Example 1, 183 g of an aqueous solution of NaOH with 9.7 meq/g and 193.4 g of glycerol monochlorohydrin (1.75 mole)

are added simultaneously, removing the water progressively by azeotropic distillation.

Duration of the additions: 3 hours 40 minutes between 135° and 140° C.

5 to 10 minutes after the end of the additions, the reaction mixture is cooled down to around 80° C., the reaction mass is taken up with 300 ml of isopropanol, the residual alkalinity is neutralized with 6N hydrochloric acid, and the sodium chloride formed is filtered off.

The solvents are removed under reduced pressure. 228 g of a light brown product are thus obtained which contain 12.6% of 1,2-dodecanediol (determination by gas chromatography). 100 g of the product thus obtained are heated under a pressure of 266.6 Pa (2 mm of Hg) to partially remove the dodecanediol. The residual content is then 8.8%.

The final product is completely soluble in water.

The cloud point, which is measured at a concentration of 0.5% by weight in water containing 25% by weight of sodium chloride, is greater than 100° C. A 10% solution of active substances remains perfectly clear above 4° C.

EXAMPLE 3

40 g of commercial xylene are added to 44 g (0.2 mole) of nonylphenol. The mixture is heated to 140° C. and then, at that temperature, 124.7 g of an aqueous solution of NaOH with 9.7 meq/g and 132.6 g (1.2 mole) of glycerol monochlorohydrin are introduced simultaneously, under a light stream of nitrogen, while removing the water by azeotropic distillation using a Dean-Stark apparatus.

Duration of the additions: 4 hours.

After cooling to about 70° C., the reaction mass is taken up with 170 g of methanol. The temperature is maintained in the region of the reflux temperature for 30 minutes, then it is cooled, and sodium chloride is filtered off at room temperature.

Xylene and methanol are distilled off under reduced pressure. The product obtained appears in the form of a vitreous, amber, transparent mass, which is sticky to the touch. It is completely soluble in water.

The cloud point, which is measured at a concentration of 0.5% by weight in water containing 25% by weight of NaCl, is greater than 100° C.

EXAMPLE 4

58 g of commercial xylene are added to 57.6 g (0.1 mole) of a mixture of 2-(decyl)tetradecyl ether of polyglycerols comprising on average three units derived from glycerol, and then the mixture is heated to 140° C. under a light stream of nitrogen. 73 g of an aqueous solution of NaOH with 9.7 meq/g and 77.3 g (0.7 mole) of glycerol monochlorohydrin are then introduced simultaneously over a period of 3 hours 15 minutes, so as to constantly maintain a slight excess of NaOH in the reaction medium. The water is removed as it is formed.

Upon completion of the additions, the temperature is maintained constant for about 10 minutes while optionally distilling off a portion of the xylene.

The reaction mixture is cooled to about 80° C., and then 150 ml of isopropanol are added. Sodium chloride is separated off by filtration and then xylene and isopropanol are removed by heating under reduced pressure.

A product is thus obtained which appears in the form of a transparent, amber paste, which is finely dispersible in water.

The cloud point, which is measured at a concentration of 5% by weight in water containing 25% of butyldiglycol, is 70° C.

EXAMPLE 5

Polycondensation of glycerol monochlorohydrin with the following mixture of compounds [A], in an 8 moles/mole ratio

$R_2 = C_{12}H_{25}$
$R_3 = 50/50$ mixture of $C_{13}H_{27}$ and $C_{15}H_{31}$
$\underline{p}$ = mean statistical value 1.16
$\underline{q}$ = mean statistical value 3.

PREPARATION OF THE MIXTURE OF COMPOUNDS [A]

72 g (0.3 mole) of 1,2-epoxyhexadecane and 80 g (0.3 mole) of 1,2-epoxyoctadecane are added to 335 g of 1-dodecanol (1.8 mole), over a period of 1 hour 15 minutes, at 150° C., in the presence of sodium methylate (0.3 equivalent).

Heating is continued for another 4 hours. The catalyst is then neutralized with hydrochloric acid and the uncondensed 1-dodecanol (238 g) is removed by heating to 170° C. under a pressure of 133 Pa (1 mm of Hg).

65 g (0.7 mole) of epichlorohydrin are then condensed onto 103 g (0.234 mole) of the product thus obtained, in the presence of $BF_3$/ether, at 55°–60° C.

The polychlorinated derivatives are then hydroxylated by heating at 180° C. in dipropyleneglycol, in the presence of potassium acetate, over a period of 4 hours. The product is then saponified and washed. After drying, a compound is obtained which has the appearance of a clear, amber, water-insoluble oil.

45 g of xylenes are added to 33.1 g (0.05 mole) of the mixture of compounds [A] thus obtained, and the mixture is then heated to 140° C.; 41.75 g of an aqueous solution of NaOH with 9.7 meq/g and 44.2 g (0.4 mole) of glycerol monochlorohydrin are then added simultaneously.

Duration of the additions: 5 hours at a temperature of 140° C. ±5.

The reaction mass is taken up with 150 g of isopropanol, the salt is separated off by filtration and the solvents are evaporated by heating under reduced pressure.

The product obtained appears in the form of a soft, amber paste which is dispersible in water. The cloud point, which is measured at a concentration of 5% in water containing 25% of butyldiglycol, is 92° C.

EXAMPLE 6

Polycondensation of glycerol monochlorohydrin with the following mixture of compounds [B], in an 8 moles/mole ratio.

$R_1$ = hydrocarbon moieties derived from lanolin alcohols
$\overline{m}$ = mean statistical value = 2.

PREPARATION OF THE MIXTURE OF COMPOUNDS [B]

Polyaddition of 185 g (2 moles) of glycerol epichlorohydrin onto 363 g of alcohols from hydrogenated lanolin (1 mole) in the presence of $BF_3/CH_3COOH$.

The polychlorinated derivatives are hydrolyzed in 550 g of dipropylene glycol, in the presence of 200 g of potassium acetate, at 180° C. After saponification and washing with water, in the presence of butanol, a yellow paste is obtained with a hydroxyl number of 5.2 meq/g.

POLYCONDENSATION OF THE MONOCHLOROHYDRIN 45 g of a commercial mixture of xylenes are added to 40.6 g of the mixture of compounds [B] thus obtained (0.07 mole), and then the mixture is heated to 140° C. under a light stream of nitrogen. 57 g of an aqueous solution of NaOH with 9.7 meq/g and 62 g (0.56 mole) of glycerol monochlorohydrin are then introduced simultaneously, while removing the water by azeotropic distillation.

Duration of the additions: 4 hours.

Upon completion of the additions, the reaction mixture is maintained for 10 minutes at a temperature of between 140° and 145° C., and then it is allowed to cool to 80° C. 150 ml of isopropanol are added and the salt formed is separated off.

The solvents are removed by heating under reduced pressure.

A brown paste of soft consistency and completely soluble in water is thus obtained.

The cloud point, which is measured at a concentration of 0.5% by weight in water containing 25% by weight of NaCl, is greater than 100° C.

EXAMPLE 7

20 g of xylene are added to 39.6 g (0.1 mole) of nonylphenol which has been polyoxyethylenated and comprises 4 ethylene oxide units, and then the mixture is heated to 145° C. under nitrogen; 51 g of a 40% aqueous solution of NaOH and 55.2 g (0.5 mole) of glycerol monochlorohydrin are then added simultaneously, while removing the water, as it is formed, by azeotropic distillation. The duration of the additions is 4 hours. The temperature is allowed to drop to 90° C. and the reaction mass is taken up with 50 g of isopropanol; the sodium chloride is filtered off and the solvent is then evaporated off under reduced pressure.

A product is obtained which appears in the form of a very viscous liquid which is soluble in water with a very slight opalescence.

The cloud point, which is measured at 0.5% in water, is 84° C.

EXAMPLE 8

858 g (3 moles) of 1,2-octadecanediol in 900 ml of xylene are heated to 90° C., until total dissolution is achieved. 15.6 g of an aqueous solution of NaOH with 9.64 meq/g (0.15 mole) are then added, and the reaction mass is heated gradually to 135°-140° C., while removing the water by azeotropic distillation.

1.089 g (10.5 moles) of an aqueous solution of NaOH with 9.64 meq/g and 1.179 g (10.5 moles) of 98.4% pure glycerol monochlorohydrin are then introduced simultaneously, using two dropping funnels.

The water is removed as it forms.

The duration of the additions are respectively 3 hours 30 minutes and 3 hours 40 minutes for the aqueous solution of NaOH and for glycerol monochlorohydrin.

The temperature and stirring are continued for 30 minutes after the last addition.

The reaction mass is cooled to about 80° C., and it is taken up with 3.2 liters of isopropanol. Cooling is continued to 30° C., the alkalinity is neutralized with 33% hydrochloric acid, and the salt formed is filtered off on sintered glass. The precipitate is rinsed with isopropanol.

The solvents are removed by distillation under reduced pressure.

A product is thus obtained which appears in the form of a brown wax of hard consistency and soluble in water above 51° C.

EXAMPLE 9

40 g of xylene and 1 g of an aqueous solution of NaOH at 9.65 meq/g are added to 77.6 g (0.2 mole) of polyglycerol oleyl ether comprising 2 moles of glycerol.

Then, 62.2 g (600 meq) of an aqueous solution of NaOH with 9.65 meq/g and 66.3 g (0.6 mole) of glycerol monochlorohydrin are introduced simultaneously under a nitrogen atmosphere, at 145°/150° C., while removing the water by azeotropic distillation.

Duration of the additions: 2 hours.

The reaction mass is then taken up with 100 g of isopropanol; the alkalinity is neutralized with approximately 3N hydrochloric acid, and the salt formed is filtered off by filtration on sintered glass. The precipitate is rinsed with isopropanol.

The solvents are removed by heating under reduced pressure (30 mm of Hg).

119 g of an amber product are thus obtained, having the consistency of a soft paste and which is solubilized in water with a slight opalescence.

I claim:

1. A single stage process for preparing a water-soluble or water-dispersible polyglycerolated nonionic surfactant comprising condensing glycerol monochlorohydrin with a (poly)hydroxylated organic compound selected from the group consisting of an alkylphenol, a 1,2-alkanediol, a polyethoxylated fatty alcohol, a polyethoxylated alkylphenol and a (poly) glycerol ether in the presence of a strong base, and in the presence of an aromatic solvent at a temperature below 150° C., the mole ratio of said glycerol monochlorohydrin to said polyhydroxylated compound being greater than 1 and the said aromatic solvent being present in an amount ranging from 0.4 to 1.5 parts by weight per 1 part by weight of said (poly)hydroxylated organic compound, and removing water as it forms by distillation.

2. Process according to claim 1, wherein the (poly)-hydroxylated compound is selected from the group consisting of octylphenol, nonylphenol, $C_8$ to $C_{20}$ 1,2-alkanediols, polyethoxylated fatty alcohols containing 8 to 24 carbon atoms in the lipophilic chain, polyethoxylated octyl- and nonylphenols containing from 2 to 20 oxyethyl units, (poly)glycerol ethers of formula:

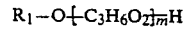
$$R_1-O\text{-}(C_3H_6O_2)_{\overline{m}}H \qquad (III)$$

in which $R_1$ denotes an octyl- or nonylphenyl radical, a $C_8$ to $C_{24}$ aliphatic radical, or an aliphatic or cycloaliphatic radical which can contain from 18 to 30 carbon atoms and is derived from hydrogenated lanolin or lanolin alcohols, and m denotes 1 or 2, or an average statistical number from 1.5 to 8, (poly)glyerol ethers of formula:

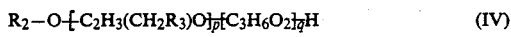  (IV)

in which $R_2$ denotes an octylphenyl or nonylphenyl radical or a $C_8$ to $C_{24}$ aliphatic radical, and $R_3$ denotes a $C_7$ to $C_{17}$ aliphatic radical or a $C_8$ to $C_{20}$ alkoxy radical, with the proviso that the sum of the carbon atoms in $R_1$ and $R_2$ is between 16 and 32; p denotes the number 1 or an average statistical value of between 1.5 and 2, and q denotes the number 1 or 2 or an average statistical value of 1.5 to 8.

3. Process according to claim 1 wherein the mole ratio of glycerol monochlorohydrin to the (poly)hydroxylated compound is equal to or greater than 2.

4. Process according to claim 1 wherein the aromatic solvent is selected from the group consisting of toluene, cumene, orthoxylene, metaxylene, para-xylene and a mixture thereof.

5. Process according to claim 4, characterized in that the aromatic solvent is the commercial mixture of the three xylene isomers.

6. Process according to claim 1 wherein an aqueous sodium hydroxide or potassium hydroxide solution is used as the strong base.

7. Process according to claim 1 wherein the condensation is performed at a temperature of 120° to 145° C.

8. Process according to claim 1 wherein the strong base is used in a stoichiometric quantity with respect to the glycerol monochlorohydrin, this quantity being from 5 to 10 mole % higher with respect to the (poly)hydroxylated compound.

9. Process according to claim 1 wherein the reaction is carried out under an inert atmosphere, and at the end of the reaction, the reaction mass is taken up in an alcohol having from 1 to 4 carbon atoms, the salt formed is filtered off and the solvents are removed by distillation.

10. Process according to claim 9, wherein the alcohol is selected from the group consisting of methanol, isopropanol and butanol.

11. The process of claim 1 wherein said (poly)hydroxylated compound is a $C_8$ to $C_{20}$ 1,2-alkanediol.

12. The process of claim 11 wherein said alkanediol is 1,2-dodecanediol.

* * * * *